(12) United States Patent
Hacquard

(10) Patent No.: US 11,197,775 B2
(45) Date of Patent: Dec. 14, 2021

(54) ANATOMICAL RING DEVICE WITH DIFFERENTIALLY STRETCHABLE SECTIONS

(71) Applicant: Health Devices Corporation, North Hollywood, CA (US)

(72) Inventor: Francois Hacquard, San Pedro, CA (US)

(73) Assignee: Health Devices Corporation, North Hollywood, CA (US)

( * ) Notice: Subject to any disclaimer, the term of this patent is extended or adjusted under 35 U.S.C. 154(b) by 70 days.

(21) Appl. No.: 16/712,028

(22) Filed: Dec. 12, 2019

(65) Prior Publication Data

US 2021/0177640 A1  Jun. 17, 2021

(51) Int. Cl.
*A61F 5/41* (2006.01)
(52) U.S. Cl.
CPC .......... *A61F 5/41* (2013.01); *A61F 2005/411* (2013.01); *A61F 2005/414* (2013.01); *A61F 2005/417* (2013.01)
(58) Field of Classification Search
CPC ............................ A61F 5/41; A61F 2005/411; A61F 2005/414; A61F 2005/415; A61H 19/32; A61H 19/50; A61H 2205/087
See application file for complete search history.

(56) References Cited

U.S. PATENT DOCUMENTS

| | | | |
|---|---|---|---|
| 5,873,813 A | 2/1999 | Weiss | |
| 6,050,931 A * | 4/2000 | Russell | ................... A61N 2/06 600/15 |
| 7,674,225 B2 | 3/2010 | Shelyakov et al. | |
| 2003/0024536 A1 | 2/2003 | Bagby | |
| 2004/0236179 A1 * | 11/2004 | Egretier | .................... A61F 5/41 600/38 |
| 2006/0094926 A1 | 5/2006 | Forsell | |
| 2010/0179379 A1 * | 7/2010 | Park | ......................... A61F 5/41 600/41 |

FOREIGN PATENT DOCUMENTS

| | | |
|---|---|---|
| JP | 2002085437 | 3/2002 |
| KR | 20030072307 | 9/2003 |
| KR | 20130006750 | 11/2013 |
| KR | 201516524 | 5/2015 |

* cited by examiner

*Primary Examiner* — Samuel G Gilbert

(57) ABSTRACT

An anatomical ring device for attachment to a penis includes a closed ring body defining an interior opening that is shaped and sized to receive a penis. The ring body may include two or more high-stretch sections separating two or more low-stretch sections of the ring body. The low-stretch sections may include a material that is substantially less stretchable than a material that comprises the high-stretch sections. The low-stretch sections may include two or more stiffeners disposed in the ring body. The high-stretch sections may include areas of the ring body that are situated between the stiffeners.

19 Claims, 3 Drawing Sheets

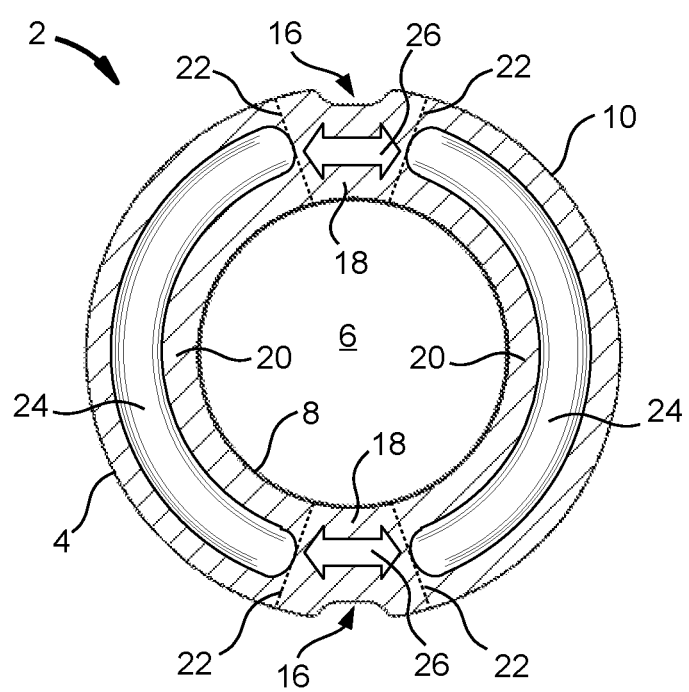
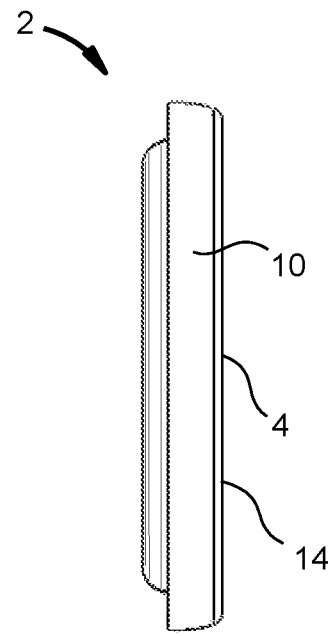
FIG. 5
FIG. 6
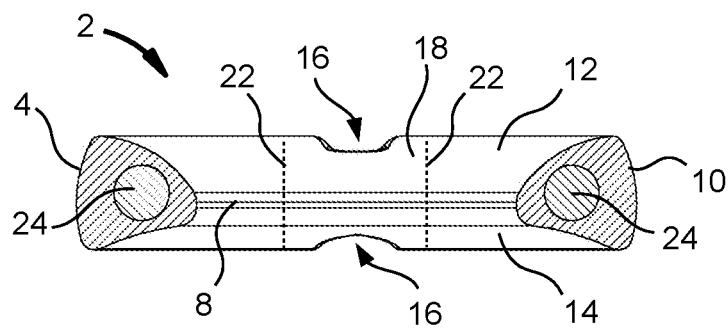
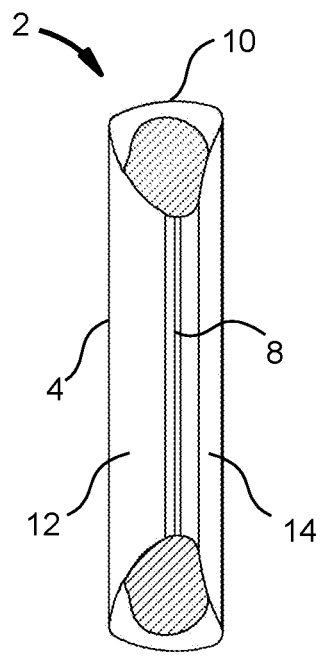
FIG. 7
FIG. 8

ANATOMICAL RING DEVICE WITH DIFFERENTIALLY STRETCHABLE SECTIONS

BACKGROUND

1. Field

The present disclosure relates to anatomical devices that enhance sexual performance and/or treat impotence in human males. More particularly, the disclosure concerns an anatomical ring device for attachment to the base of a human penis.

2. Description of the Prior Art

By way of background, anatomical rings have been developed for enhancing male sexual performance and/or treating conditions such as erectile dysfunction. Such devices are sometimes colloquially referred to as penis rings. Penis rings are of generally circular configuration and designed to slide onto a penis, until the base is reached, usually when the penis is already fully or partially erect. In some applications, the ring is situated in front of the scrotum. In other applications, the ring is situated behind the scrotum. The ring is sized to apply a compressive force that constricts the penis. Much like a valve, this constriction prevents the blood that engorges the erectile tissue from flowing away from the penis. In this way, a penis ring can increase the strength of the erection and/or help sustain it for a longer period of time than would otherwise be possible.

There are two commonly-used types of penis ring; namely, those made entirely of a rigid material such as metal, and those made entirely of an elastomeric material such as silicone rubber. Rigid penis rings are generally more effective than elastomeric rings. Elastomeric penis rings are generally more comfortable than rigid rings.

The effectiveness of rigid penis rings stems from their ability to maintain good compression on the penis due to their hardness and size invariance. However, these characteristics also present several disadvantages. If the ring fits too loosely around the base of the penis, it may not be effective. If the ring fits too tightly on the base of the penis, it may be uncomfortable or even painful to wear. Even if the ring is correctly sized for the base of the penis, the anatomy of the penis may be such that the ring is too small to fit over the head or mid-shaft region of the penis, or to be maneuvered past the scrotum. This may result in discomfort or pain when putting on the ring.

The comfort of elastomeric penis rings stems from their ability to flexibly accommodate variations in penis girth and scrotum size due to their softness and dimensional variability. However, these characteristics also present several disadvantages. Such rings may be too soft for some users, and may be too flexible to maintain adequate compression on the penis. In that case, the ring may not achieve the desired result.

Applicant submits that it would be desirable to provide an anatomical ring for attachment to a penis that offers the effectiveness of rigid penis rings while providing the comfort of elastomeric rings.

SUMMARY

An anatomical ring device for attachment to a penis includes a closed ring body defining an interior opening that is shaped and sized to receive a penis. The ring body may include two or more high-stretch sections separating two or more low-stretch sections of the ring body. The low-stretch sections may include a material that is substantially less stretchable than a material that comprises the high-stretch sections.

In an embodiment, the high-stretch sections may include an elastomeric material.

In an embodiment, the low-stretch sections may include a substantially rigid material.

In an embodiment, the entire ring body may include an elastomeric material and the low-stretch sections may include stiffeners disposed in the elastomeric material.

In an embodiment, there may be two low-stretch sections separated by two high-stretch sections.

In an embodiment, there may be three low-stretch sections separated by three high-stretch sections.

In an embodiment, there may be four low-stretch sections separated by four high-stretch sections.

In an embodiment, the high-stretch sections may be visually distinct from the low-stretch sections.

In an embodiment, the high-stretch sections may include cross-sectional areas that are different from cross-sectional areas of the low-stretch sections.

In an embodiment, the high-stretch sections may include cross-sectional areas that are smaller than cross-sectional areas of the high-stretch sections.

In an embodiment, each high-stretch section may include a groove formed on an outer edge surface of the ring body.

In an embodiment, the ring body may include an inner edge surface that defines the interior opening, an outer edge surface laterally spaced from the inner edge surface, a first face surface, and a second face surface axially spaced from the first face surface.

In an embodiment, the inner edge surface may be axially thinner than the outer edge surface.

In an embodiment, the ring body may include a generally three-sided cross-sectional configuration.

In an embodiment, the first face surface may be generally convex to accommodate a user's fingers during device installation.

In an embodiment, the second face surface may be generally concave to accommodate a user's thumbs during device installation.

In an embodiment, the stiffeners may each include a generally arcuate lengthwise configuration.

In an embodiment, the stiffeners may each include a generally circular cross-sectional configuration.

In another aspect, an anatomical ring device for attachment to a penis may include a closed ring body defining an interior opening that is shaped and sized to receive a penis. Two or more stiffeners may be form part of the ring body. The stiffeners may be separated from each other by gaps defining high-stretch sections of the ring body that are disposed between the stiffeners.

In a further aspect, an anatomical ring device for attachment to a penis may include an elastomeric closed ring body defining an interior opening that is shaped and sized to receive a penis. The ring body may include two or more high-stretch sections separating two or more low-stretch sections of the ring body. The low-stretch sections may include stiffeners fully embedded inside the ring body so as to be hidden from view. The stiffeners may be separated from each other by gaps that define the high-stretch sections.

BRIEF DESCRIPTION OF THE DRAWINGS

The foregoing and other features and advantages will be apparent from the following more particular description of example embodiments, as illustrated in the accompanying Drawings.

FIG. 5 is a combined cross-sectional and plan view of the anatomical ring device of FIG. 1 taken along line 5-5 in FIG. 4, showing a cross-sectional view of an elastomeric ring body and a plan view of two stiffeners disposed in the ring body.

FIG. 6 is an edge view of the combined cross-sectional and plan view of FIG. 5.

FIG. 7 is a cross-sectional view taken along line 7-7 in FIG. 3.

FIG. 8 is a cross-sectional view taken along line 8-8 in FIG. 3.

DETAILED DESCRIPTION OF EXAMPLE EMBODIMENTS

Figure 1:
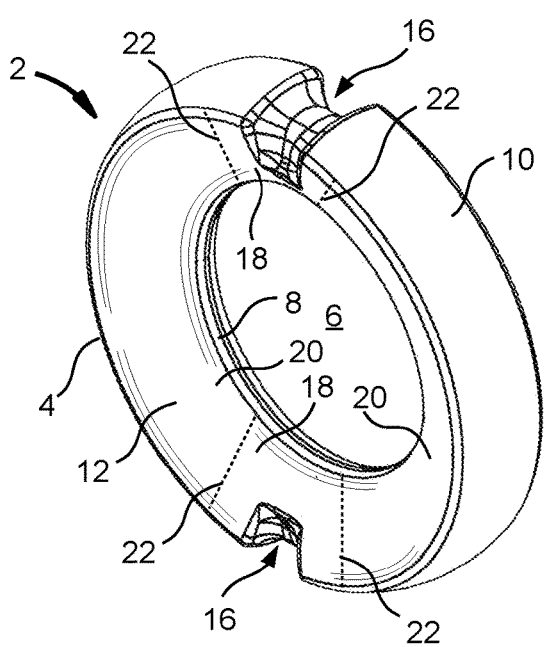
FIG. 1 is perspective view showing a front face of an anatomical ring device constructed in accordance with an embodiment of the present disclosure.

Turning now to the figures, wherein like reference numerals represent like elements in all of the several views, FIGS. 1-4 depict an anatomical ring device 2 for attachment to a human penis (not shown). In the illustrated embodiment, the ring device 2 includes a closed ring body 4 that may be formed as an uninterrupted hoop or band of generally toroidal shape. The ring body 4 may include an interior opening 6 that is shaped and sized to receive the penis. The interior opening 6 may be defined by a generally circular inner edge surface 8 that may engage the base of the penis during use. A generally circular outer edge surface 10 may be spaced laterally (radially) outwardly from the inner edge surface 8. The ring body 4 may further include first and second face surfaces, namely, a front face surface 12 (FIG. 1) that may face away from the user's torso during use, and a rear face surface 14 (FIG. 2) that is axially spaced from the front face surface and may face the user's torso during use. As used herein, the terms "laterally" and "lateral" refers to directions that are parallel to the plane of FIG. 3, and the terms "axially" and "axial" refer to a direction that is normal to the plane of FIG. 3.

In the illustrated embodiment, the interior opening 6 of the ring body 4 may have a diameter ranging between 1.5-2.5 inches (which should be suitable for most users), with other sizes also being possible. The radial thickness of the ring body 4, as measured by the lateral spacing between the inner edge surface 8 and the outer edge surface 10, may range between 0.5-0.75 inches, with other radial dimensions also being possible. The axial thickness of the ring body 4, as measured axially along the outer edge surface 10, may range between 0.375-0.75 inches, with other axial dimensions also being possible.

It will be appreciated that although the ring device 2 shown in FIGS. 1-4 includes a ring body 4 that may be shaped as a toroid, other embodiments (not shown) may utilize different ring body shapes and configurations. For example, instead of the interior opening 6 being generally circular, it could be generally oblong (e.g., an oval), generally polygonal (e.g., shaped as a regular or irregular polygon of three sides or more), or implemented with any other shape that is compatible with the cross-sectional configuration of a typical human penis.

Figure 2:
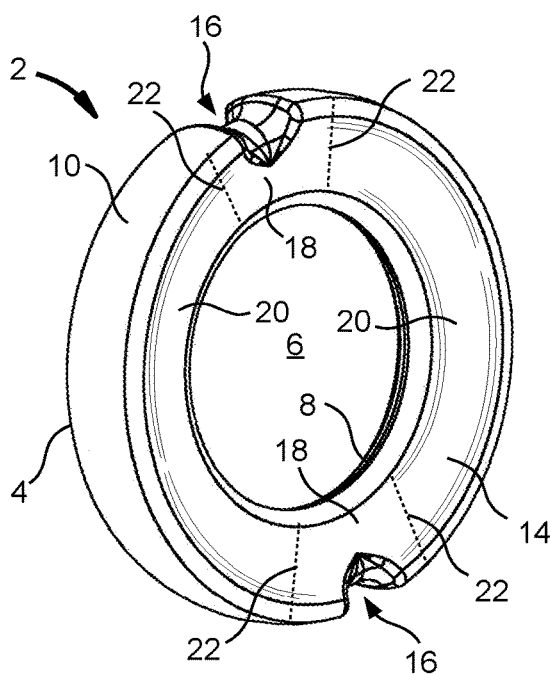
FIG. 2 is a perspective view showing a rear face of the anatomical ring device of FIG. 1.
Figure 3:
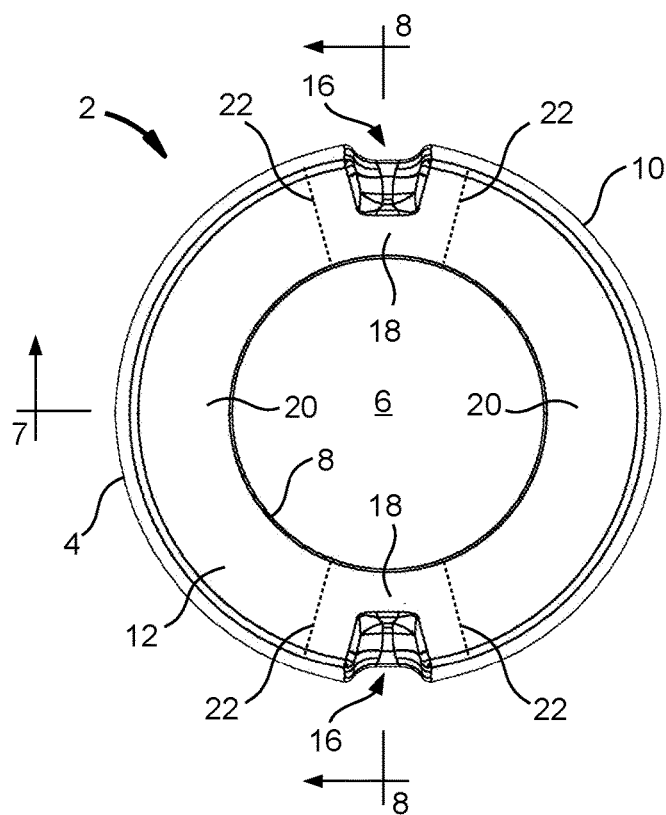
FIG. 3 is a plan view of the front face of the anatomical ring device of FIG. 1.
Figure 4:
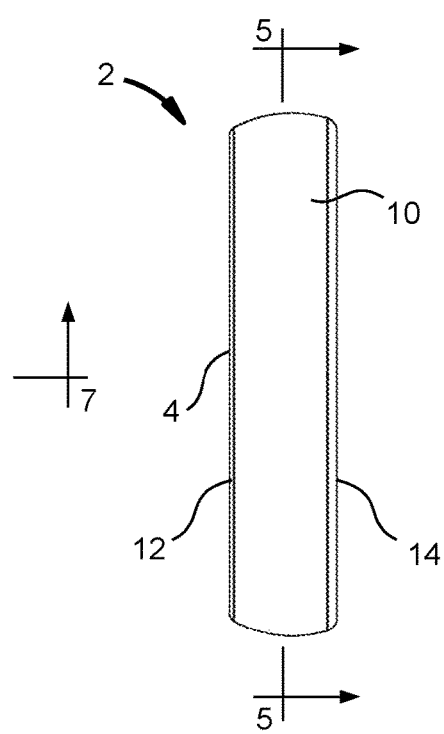
FIG. 4 is an edge view of the anatomical ring device of FIG. 1.

The shape of the outer edge surface 10 of the ring body 4 may also be varied, perhaps to an even greater degree than the inner edge surface 8 insofar as the outer edge surface is not constrained by having to engage the penis during use. Thus, although the outer edge surface 10 may correspond in shape to the inner edge surface 8, there is no requirement that it do so. This is illustrated in FIGS. 1-3, which depict the outer edge surface 10 being formed with a pair of grooves 16 disposed 180 degrees apart from each other. The purpose of the grooves 16 is discussed in more detail below.

Although not shown, the outer edge surface 10 may also be formed with one or more auxiliary structures, such as handles to facilitate stretching the ring body 4 during placement on the penis. In other designs, the outer edge surface 10 could be provided with an auxiliary structure in the form of a housing that accommodates, for example, a vibrator mechanism. In such embodiments, it will be appreciated that the interior opening 6 might not be centered on the ring body 4. It could be offset relative to the exterior contour of the ring body 4 as defined by the outer edge surface 10. The ring body 4 could also have localized areas of increased or decreased axial dimension formed on the front face surface 12 or the rear face surface 14.

As shown in FIGS. 1-3, the ring body 4 may include two or more high-stretch sections 18 of the ring body separating two or more low-stretch sections 20 of the ring body. The low-stretch sections 20 are designed to impart relatively unyielding compressive forces on the penis in a manner similar to a rigid penis ring. The high-stretch sections 18 are designed to allow the interior opening 6 to flexibly adjust in size and shape during installation and use in a manner similar to an elastomeric penis ring. In this way, the ring 2 provides a hybrid penis ring design that combines the advantages of both rigid rings and elastomeric rings while minimizing, if not eliminating, the disadvantages of each.

Dashed lines 22 are depicted in FIGS. 1-3 to illustrate example boundaries of the high-stretch and low-stretch sections 18 and 20. The low-stretch sections 20 may be formed of a material that is substantially less circumferentially stretchable than a material that comprises the high-stretch sections 18. As used herein, circumferential stretchability represents a physical property of the ring 2 that resists changes in the size and shape of the interior opening 6. Mathematically speaking, for a closed hoop or band like the ring 2, circumferential stretchability is inversely proportional to circumferential stiffness (also known as hoop stiffness), which is a function of circumferential stress (also known as hoop stress)/circumferential strain (also known as hoop strain).

It is desirable that the circumferential stiffness of the low-stretch sections 20 be substantially higher than the circumferential stiffness of the high-stretch sections 18. In an embodiment, this may be achieved by forming the entire ring body 4 of an elastomeric material that provides the relatively high circumferential stretchability (low circumferential stiffness) required for the high-stretch sections 18, and forming the low-stretch sections 20 by incorporating stiffeners with relatively low circumferential stretchability (high circumferential stiffness) within selected regions of the ring body's elastomeric material.

The foregoing technique is illustrated in FIGS. 5-8, which depict the ring body 4 having disposed therein two internal stiffeners 24. The stiffeners 24 may be separated from each other by gaps or gap areas that define the high-stretch sections 18. In this embodiment, the ring body 4 may be formed from any suitable elastomeric material, such as a rubber of the type normally used in the manufacture of elastomeric penis rings. By way of example only, silicone rubber (polysiloxane) having a durometer hardness of shore 10A-30A may be used. The stiffeners 24 may be formed of any suitable material, which may be substantially rigid in nature, such as metal, plastic, ceramic or other materials that will not noticeably stretch, flex or otherwise deform during normal use of the ring device 2 for human erectile enhancement.

FIGS. 5-8 depict an embodiment in which the stiffeners 24 are fully embedded within the ring body 4, and thus hidden from view. However, other embodiments may be implemented in which the stiffeners 24 are not fully embedded in the ring body, and are instead partially exposed to view. In a partially exposed embodiment, the ring body 4 could be formed from a relatively soft elastomeric material that covers a portion of each stiffener 24, but not the entirety thereof. One advantage of fully or partially embedding the stiffeners 24 within the ring body 4 is that the stiffeners can be spaced laterally (radially) outwardly from the inner edge 8 of the ring body 2, with the inner edge 8 itself consisting solely of the relatively soft material of the ring body. This further increases ring comfort and fit in a manner similar to elastomeric penis rings.

As best shown in FIG. 5, the stiffeners 24 may each include a generally arcuate lengthwise configuration so as to be compatible with the ring body 4 being generally toroidal in the illustrated embodiment. It will be appreciated that if the ring body 4 has other configurations, the stiffeners 24 may have a different lengthwise configuration that corresponds to the ring body configuration. As best shown in FIG. 7, the stiffeners 24 may each include a generally circular cross-sectional configuration, with other cross-sectional configurations also being possible.

As can be seen in FIGS. 1-3, 5 and 7, the ring body 4 may be configured so that the high-stretch sections 18 are visually distinct from the low-stretch sections 20. For example, each high-stretch section 18 may include the previously-mentioned grooves 16 formed on the outer edge surface 10 of the ring body 4. The grooves may be of any desired configuration, size and number. In the illustrated embodiment, there is one groove 16 in each high-stretch section 18. As best shown in FIGS. 1 and 2, each groove 16 may be formed as a generally saddle-shaped trough. The grooves 16 may be thought of as having a variable depth dimension that extends in the lateral (radial) direction of the ring body 4, a variable width dimension that extends in the axial direction of the ring body, and a variable length dimension that extends in the lengthwise circumferential stretching direction of the high-stretch sections 18. Although not shown, similar grooves could be formed on the inner edge surface 8 of the ring body 4, either in addition to or in lieu of the grooves 16 on the outer edge surface 10.

Advantageously, the grooves 16 provide a visual indication of the locations of the high-stretch sections 18. Knowing the locations of the high-stretch sections 18 may help the user determine the direction in which stretching occurs when installing the ring 2. This stretching direction, which is along the lengthwise (circumferential) dimension of the high-stretch sections 18, is indicated by the arrows 26 in FIG. 5. Using the grooves 16 as a guide, the user may intuitively grasp the low-stretch sections 20 of the ring body 4 (e.g., approximately midway between the grooves) and pull the ring body 4 apart in the stretching direction 26. This will increase the size of the interior opening 6, allowing the user to easily pull the ring 2 over the penis. It will be appreciated that the stretching direction 26 shown in FIG. 5 represents the approximate direction of the previously-discussed circumferential stresses within the ring body 4 that are resisted by the circumferential stiffness of the high-stretch sections 18 when the size of the interior opening 6 is increased.

It will be appreciated that other forms of stretching-direction indicia may be provided on the ring 2, either as an alternative or in addition to the grooves 16. For example, verbiage, arrows, and/or other markings may be displayed on the outside of the ring body 4.

A further advantage of the grooves 16 is that they provide localized reductions in the cross-section of the ring body 4. The high-stretch sections 18 will thereby have cross-sectional areas that are different (i.e., smaller) than the cross-sectional areas of the low-stretch sections 20. The reduction in cross-sectional area of the high-stretch sections 18 will be dictated by the depth, width, length of the grooves 16. By controlling the geometry of the grooves 16, the circumferential stretchability of the high-stretch sections 18 may be increased as necessary to achieve optimal operational characteristics, namely, a ring that is comfortable to wear and easy to install, yet firm enough to promote penile engorgement.

As previously described in connection with FIGS. 1-3, the ring body 4 may include an inner edge surface 8 that defines the interior opening 6, an outer edge surface 10 laterally (radially) spaced from the inner edge surface, a front face surface 12 and a rear face surface 14. It will be appreciated that the ring body 4 may have a variety of cross-sectional configurations. In the illustrated embodiment, and as best shown in FIGS. 7 and 8, the inner edge surface 8 may be axially thinner than the outer edge surface 10, such that the ring body has a generally three-sided triangular cross-sectional configuration. This configuration may aid in promoting penile engorgement due to the relatively thin inner edge surface 8 focusing the constrictive force of the ring 2 onto a relatively small area of the penis, thereby increasing the constrictive pressure at the contact site (which is a function of force/area). On the other hand, as previously mentioned, the relative softness of the stretchable material that forms the inner edge surface 8 will contribute to increased comfort and superior fit.

It will also be seen in FIGS. 7 and 8 that the front face surface 12 of the ring body 4 may be generally convex and the rear face surface 14 may be generally concave. As previously described, the front face surface 12 may face away from the user's torso during use, and a rear face surface 14 may face the user's torso during use. It will be appreciated that forming the front face surface 12 to be generally convex may assist in accommodating the user's fingers during device installation. Similarly, forming the rear face surface 14 to be generally concave may assist in accommodating the user's thumbs during device installation. The combined effect will be to increase the ease of ring installation.

Figure 9:
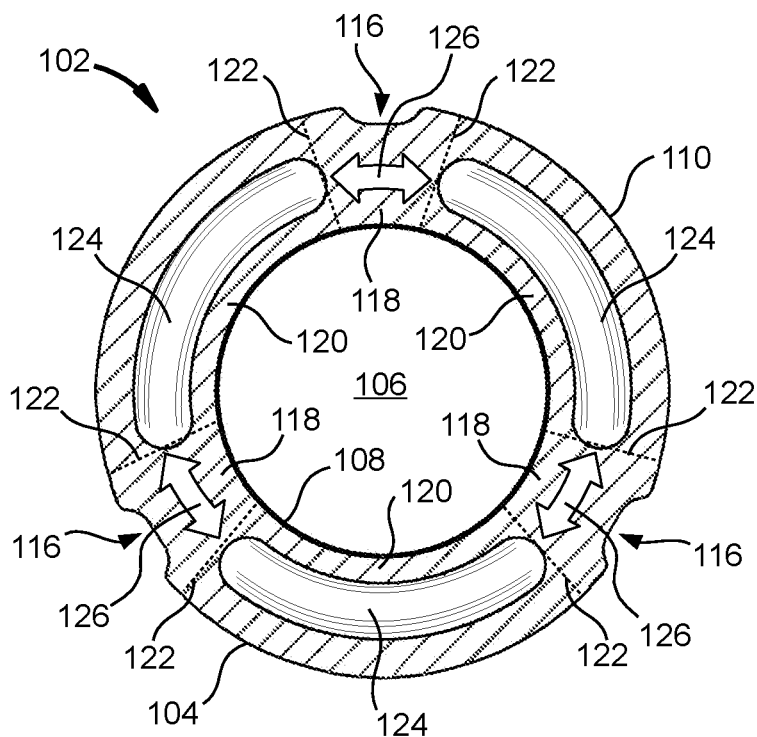
FIG. 9 is a combined cross-sectional and plan view of an anatomical ring device in accordance with another embodiment of the present disclosure, showing a cross-sectional view of an elastomeric ring body and a plan view of three stiffeners disposed within the ring body.

Turning now to FIG. 9, an anatomical ring 102 is shown that may be constructed in accordance with a further embodiment. This embodiment is similar in many respects to the anatomical ring 2 of FIGS. 1-8, as indicated by the use of corresponding reference numbers incremented by 100. However, instead of having two stiffener elements 24, as found in the ring 2 of the first embodiment, the ring 102 of the current embodiment utilizes three stiffener rings 124. This will result in the ring 102 having three high-stretch sections 118 and three low-stretch sections 120.

Figure 10:
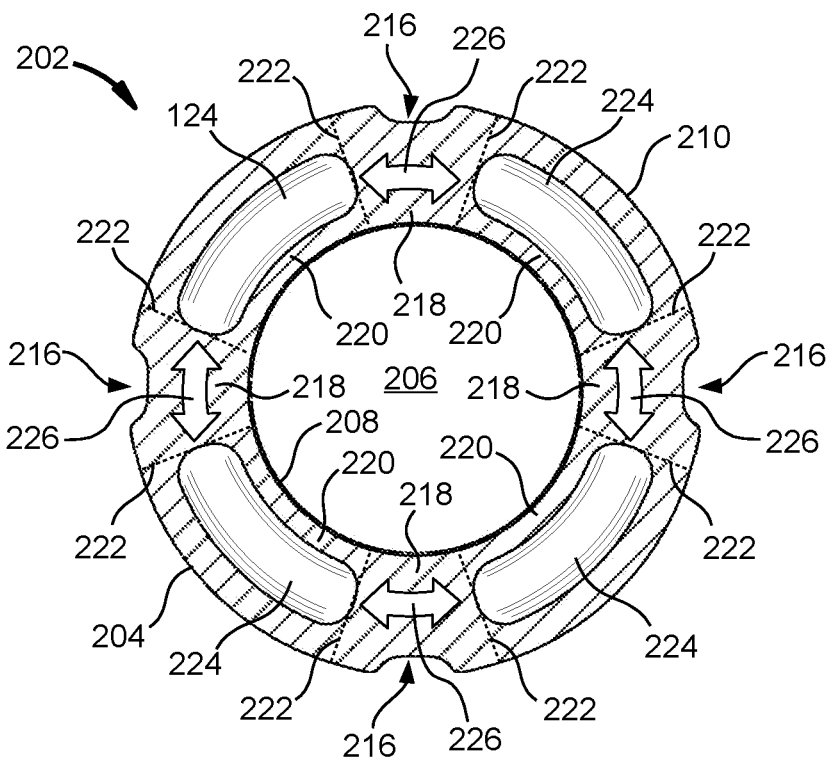
FIG. 10 is a combined cross-sectional and plan view of an anatomical ring device in accordance with another embodiment of the present disclosure, showing a cross-sectional view of an elastomeric ring body and a plan view of four stiffeners disposed within the ring body.

Turning now to FIG. 10, an anatomical ring 202 is shown that may be constructed in accordance with a further embodiment. This embodiment is also similar in many respects to the anatomical ring 2 of FIGS. 1-8, as indicated by the use of corresponding reference numbers incremented by 200. However, instead of having two stiffener elements 24, as found in the ring 2 of the first embodiment, the ring 202 of the current embodiment utilizes four stiffener rings 224. This will result in the ring 202 having four high-stretch sections 218 and four low-stretch sections 220.

It will be appreciated that embodiments of anatomical rings may be implemented with additional high-stretch and low-stretch sections.

Accordingly, an anatomical ring device for attachment to the base of a human penis has been disclosed. Although various example embodiments have been shown and described, it should be apparent that many variations and alternative embodiments could be implemented in accordance with the disclosure. It is understood, therefore, that the invention is not to be in any way limited except in accordance with the spirit of the appended claims and their equivalents.

What is claimed is:

1. An anatomical ring device for attachment to a penis, comprising:
    a closed ring body defining an interior opening that is shaped and sized to receive a penis;
    the ring body comprising two or more high-stretch sections separating two or more low-stretch sections of the ring body;
    the low-stretch sections comprising a material that is substantially less stretchable than a material that comprises the high-stretch sections;
    wherein the entire ring body comprises an elastomeric material and the low-stretch sections comprise stiffeners disposed in the elastomeric material; and
    wherein the stiffeners each comprise a generally arcuate lengthwise configuration.

2. The device of claim 1, wherein the high-stretch sections comprise an elastomeric material.

3. The device of claim 1, wherein the low-stretch sections comprise a substantially rigid material.

4. The device of claim 1, wherein the stiffeners each comprise a generally circular cross-sectional configuration.

5. The device of claim 1, wherein there are two low-stretch sections separated by two high-stretch sections.

6. The device of claim 1, wherein there are three low-stretch sections separated by three high-stretch sections.

7. The device of claim 1, wherein there are four low-stretch sections separated by four high-stretch sections.

8. The device of claim 1, wherein the high-stretch sections are visually distinct from the low-stretch sections.

9. The device of claim 1, wherein the high-stretch sections comprise cross-sectional areas that are different from cross-sectional areas of the low-stretch sections.

10. The device of claim 1, wherein the high-stretch sections comprise cross-sectional areas that are smaller than cross-sectional areas of the low-stretch sections.

11. The device of claim 1, wherein each said high-stretch section comprises a groove formed on an outer edge surface of the ring body.

12. The device of claim 1, wherein the ring body comprises an inner edge surface that defines the interior opening, an outer edge surface laterally spaced from the inner edge surface, a first face surface, and a second face surface axially spaced from the first face surface.

13. The device of claim 12, wherein the inner edge surface is axially thinner than the outer edge surface.

14. The device of claim 12, wherein the ring body comprises a generally three-sided cross-sectional configuration.

15. The device of claim 12, wherein the first face surface is generally convex to accommodate a user's fingers during device installation.

16. The device of claim 12, wherein the second face surface is generally concave to accommodate a user's thumbs during device installation.

17. An anatomical ring device for attachment to a penis, comprising:
    a closed ring body defining an interior opening that is shaped and sized to receive a penis;
    the ring body comprising two or more high-stretch sections separating two or more low-stretch sections of the ring body;
    the low-stretch sections comprising a material that is substantially less stretchable than a material that comprises the high-stretch sections; and
    wherein the high-stretch sections are visually distinct from the low-stretch sections.

18. An anatomical ring device for attachment to a penis, comprising:
    a closed ring body defining an interior opening that is shaped and sized to receive a penis;
    the ring body comprising two or more high-stretch sections separating two or more low-stretch sections of the ring body;
    the low-stretch sections comprising a material that is substantially less stretchable than a material that comprises the high-stretch sections; and
    wherein the high-stretch sections comprise cross-sectional areas that are different from cross-sectional areas of the low-stretch sections.

19. An anatomical ring device for attachment to a penis, comprising:
    a closed ring body defining an interior opening that is shaped and sized to receive a penis;
    the ring body comprising two or more high-stretch sections separating two or more low-stretch sections of the ring body;
    the low-stretch sections comprising a material that is substantially less stretchable than a material that comprises the high-stretch sections; and
    wherein each high-stretch section comprises a groove formed on an outer edge surface of the ring body.

* * * * *